United States Patent

Walsh et al.

[11] 4,044,074
[45] Aug. 23, 1977

[54] FLAME RETARDANT POLYCARBOXY ALKYL AND ARYL PHOSPHONATES

[75] Inventors: Edward N. Walsh, New City; Milton L. Honig, Bronx, both of N.Y.

[73] Assignee: Stauffer Chemical Company, Westport, Conn.

[21] Appl. No.: 669,004

[22] Filed: Mar. 22, 1976

[51] Int. Cl.² .............................................. C07F 9/40
[52] U.S. Cl. ............................... 260/928; 260/45.7 P; 260/930; 260/942; 260/982
[58] Field of Search ......................... 260/928, 930, 2 P

[56] References Cited

U.S. PATENT DOCUMENTS

| | | | |
|---|---|---|---|
| 3,062,788 | 11/1962 | McConnell et al. | 260/2 P X |
| 3,366,713 | 1/1968 | Morales | 260/928 |
| 3,442,982 | 5/1969 | Friedman | 260/928 X |
| 3,932,566 | 1/1976 | Reader | 260/930 |

*Primary Examiner*—Richard L. Raymond
*Attorney, Agent, or Firm*—William R. Robinson

[57] ABSTRACT

Flame retardant polycarboxy alkyl and aryl phosphonates having the structural formula:

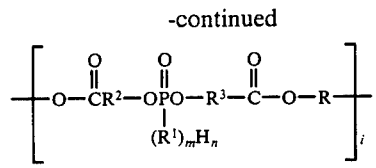

(I)

-continued

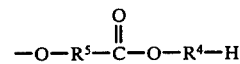

are prepared, wherein R is hydrocarbyl consisting of hydrogen and carbon and substituted hydrocarbyl including $C_2$-$C_{10}$ alkylene, arylene, $C_7$-$C_{20}$ alkylene substituted arylene, $C_3$-$C_{20}$ cycloalkylene, $C_4$-$C_{20}$ vinylene and derivatives of the foregoing containing non-labile pendant halogens, $C_1$-$C_6$ alkyls, $C_1$-$C_6$ haloalkyls, vinyls, ethers or $C_1$-$C_6$ alkyl alcohol functions. $R^1$ is hydrocarbyl consisting of hydrogen and carbon and substituted hydrocarbyl including $C_1$-$C_{10}$ alkyl, aryl, $C_7$-$C_{20}$ alkyl substituted aryl, $C_2$-$C_{10}$ alkenyl, phenoxy, $C_1$-$C_{10}$ alkoxy, aryloxy, or $C_3$-$C_{20}$ cycloalkyl, and derivatives thereof containing non-liabile pendant halogens, $C_1$-$C_6$ alkyls, $C_1$-$C_6$ haloalkyls, vinyls, ethers, or $C_1$-$C_6$ alkyl alcohol functions. $R^1$ can also be:

$$-O-R^5-\overset{\overset{O}{\|}}{C}-O-R^4-H$$

or OR⁴H wherein R⁴ has the same definition as R, and R⁴ and R can be the same or different. $R^2$, $R^3$ and $R^5$ are straight or branched $C_1$-$C_{10}$ alkylene and can be the same or different. The integer represented by i is from about 2 to about 20 and the integers represented by m and n are different and are 0 or 1.

The monomers are prepared by catalyzed transalkylation and the polymers are prepared by polycondensation of the monomers with diols or by polymeric transalkylation.

4 Claims, No Drawings

FLAME RETARDANT POLYCARBOXY ALKYL AND ARYL PHOSPHONATES

BACKGROUND OF THE INVENTION

1. Field of the Invention

The present invention relates, in general, to a method of preparing polycarboxy alkyl and aryl phosphonates and polymeric compositions thereof, and further concerns flame retardant systems incorporating said phosphorus structures.

2. The Prior Art

Polycarboxy alkylphosphonate monomers are known and are described by A. N. Pudovik et al., *Zhurnal Obschei Khimii*, Vol. 30, No. 8, pp. 2624–2630, August, 1960. Pudovik et al. disclose, among others, compositions having the structural formula:

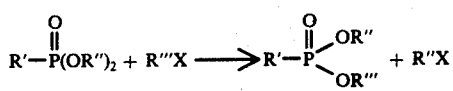

(II)

where R' is hydrogen, $CH_3$, $C_2H_5$, or $C_3H_7$.

The Pudovik et al. compounds are prepared according to the following general reaction scheme:

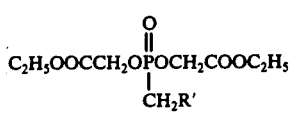

(1)

where X is I, Br or Cl and R'' and R''' are the same or different and have the same definition as R'.

Rates of reaction in the Pudovik et al. method are slow. Moreover, Pudovik et al, employed equimolar quantities of reactants; which resulted in mixtures of mono- and dicarboxy phosphonates.

SUMMARY OF THE INVENTION

In accordance with the present invention, production yields of polycarboxy alkyl and aryl phosphonates can be greatly improved by use of specific catalysts. Also, in accordance with the present invention, polymeric polycarboxy alkyl and aryl phosphonates can be made. Both the monomer and the polymer exhibit excellent flame retardancy characteristics.

In one aspect of the present invention, there is provided an improved method of preparing polycarboxy alkyl and aryl phosphonates having the structural formula:

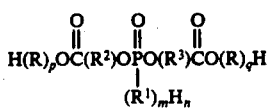

(III)

wherein R is hydrocarbyl consisting of hydrogen and carbon and substituted hydrocarbyl including $C_2-C_{10}$ alkylene, arylene, $C_7-C_{20}$ alkylene substituted arylene, $C_3-C_{20}$ cycloalkylene, $C_4-C_{20}$ vinylene and derivatives of the foregoing containing non-labile pendant halogens, $C_1-C_6$ alkyls, $C_1-C_6$ haloalkyls, vinyls, ethers or $C_1-C_6$ alkyl alcohol functions. $R^1$ is hydrocarbyl consisting of hydrogen and carbon and substituted hydrocarbyl including $C_1-C_{10}$ alkyl, aryl, $C_7-C_{20}$ alkyl substituted aryl, $C_2-C_{10}$ alkenyl, phenoxy, $C_1-C_{10}$ alkoxy, aryloxy, or $C_3-C_{20}$ cycloalkyl, and derivatives thereof containing non-labile pendant halogens, $C_1-C_6$ alkyls, $C_1-C_6$ haloalkyls, vinyls, ethers, or $C_1-C_6$ alkyl alcohol functions. $R_1$ can also be:

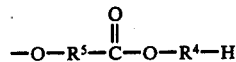

or $OR^4H$ wherein $R^4$ has the same definition as R, and $R^4$ and R can be the same or different. $R^2$, $R^3$ and $R^5$ are straight or branched $C_1-C_{10}$ alkylene and can be the same or different. The integers represented by $m$ and $n$ are different and are 0 or 1. The integers represented by $p$ and $q$ can be the same or different and are 0 or 1.

Methods of preparing new polymeric compounds also are provided in the present invention. These compounds have the structural formula:

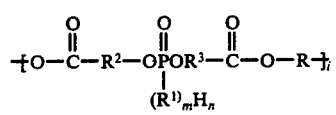

(VI)

wherein R, $R^1$, $R^2$ and $R^3$, $m$ and $n$ are as described above and $i$ is an integer from about 2 to about 20. The compounds can be prepared either by polycondensation or polymeric transalkylation.

DETAILED DESCRIPTION OF THE INVENTION

In the polycarboxy alkyl and aryl phosphonates of the present invention having the structural formula:

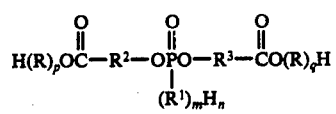

(III)

wherein R, $R^1$, $R^2$ and $R^3$, $m$, $n$, $p$ and $q$ are as defined above, exemplary R groups include but are not limited to ethylene, chloroethylene, vinylene, propylene, bromopropylene, propenylene, isopropylene, butylene, butenylene, hydroxybutylene, isobutylene, chlorobutenylyne, pentylene, hexylene, octylene, hydroxyoctylene, decylene, cyclopentylene, cylcohexylene, hydroxycyclopentylene, phenylene, methylphenylene, chlorophenylene, and others. R groups of low molecular weight, up to about 6 carbon atoms, are preferred as their low volatility allows for easy removal as ROH in subsequent esterification reactions. In the compound of Formula III, R can also be hydroxyethylene.

Exemplary $R^1$ groups include but are not limited to methyl, chloromethyl, hydroxymethyl, ethyl, chloroethyl, hydroxyethyl, vinyl, propyl, bromopropyl, propenyl, isopropyl, butyl, butenyl, hydroxybutyl, isobutyl, chlorobutyl, pentyl, hexyl, octyl, hydroxyoctyl, decyl, cyclopentyl, cyclohexyl, hydroxycyclopentyl, phenyl, methylphenyl, chlorophenyl, carbalkoxymethyl, carbalkoxyethyl, and others.

Pendant halogens on the R and R' groups include halogens having a molecular weight between 35 and 80, such as chlorine and bromine.

Exemplary $R^2$, $R^3$ and $R^5$ groups include but are not limited to methylene, ethylene, propylene, isopropylene, butylene, isobutylene, tert-butylene, pentylene, hexylene, heptylene, octylene, nonylene and decylene.

The method comprises contacting a reactant having the structural formula:

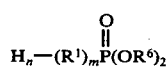   (IV)

where $R^1$, m and n are as defined above and $R^6$ is hydrocarbyl consisting of hydrogen and carbon and substituted hydrocarbyl including $C_1-C_6$ alkyl, allyl, dihaloalkyl, benzyl and derivatives thereof containing nonlabile pendant halogens: with other reactants having the structural formulas:

   (V)

and

   (VI)

wherein $R$, $R^2$ and $R^3$ and $p$ and $q$ are as defined above and $X$ is halogen having a molecular weight between about 35 and 80, in the presence of a nucleophilic catalyst selected from the group consisting of tetraethyl ammonium chloride, sodium carbonate, sodium bicarbonate, lithium chloride, and other nucleophilic salts.

The following equation (2) is representative of the reaction:

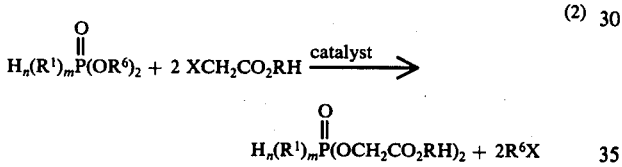   (2)

wherein R, $R^1$, $R^6X$, n and m are as defined above.

Reactants utilized in the method described above are generally employed in stoichiometric amounts, although an excess of either reactant can be used if desired. The quantity of undesired side products however, is minimized by the use of approximately stoichiometric amounts of reactants.

The method is carried out at elevated temperatures from about 120° and 250° C. and generally between about 160° and 200° C.

Reaction times can vary over relatively wide ranges and can easily be determined by one skilled in the art. Factors affecting reaction time include reactant and catalyst concentrations and temperature. Increases in temperature and catalyst concentration result in decreased reaction times. Dilute reactants require longer reaction times than concentrated reactants. Typical reaction times are from about 1 to about 12 hours.

The method described above can conveniently be effected by introducing the individual reactants and catalyst into any reaction zone that can be heated to the reaction temperature. The zone is generally provided with a condenser for removal of volatile components. A thermometer, thermocouple or other conventional means can be used to monitor temperature. The reaction can be carried out in a continuous or batch-type system as desired.

The products of the reaction are generally purified by vacuum distillation but other conventional methods such as extraction or sublimation can be used.

The identification of products can be achieved by infrared spectra, $^1H$ nuclear magnetic resonance spectra and $^{31}P$ nuclear magnetic resonance spectra, boiling point analysis and elemental analysis.

Typical yields of the above-described method of the present invention are from about 75% to about 90%, as compared to the prior art wherein the catalyst is not employed. The prior art yield is generally about 20%.

Illustrative of the compounds corresponding to structural formula (III) which can be prepared by the method of the present invention are:

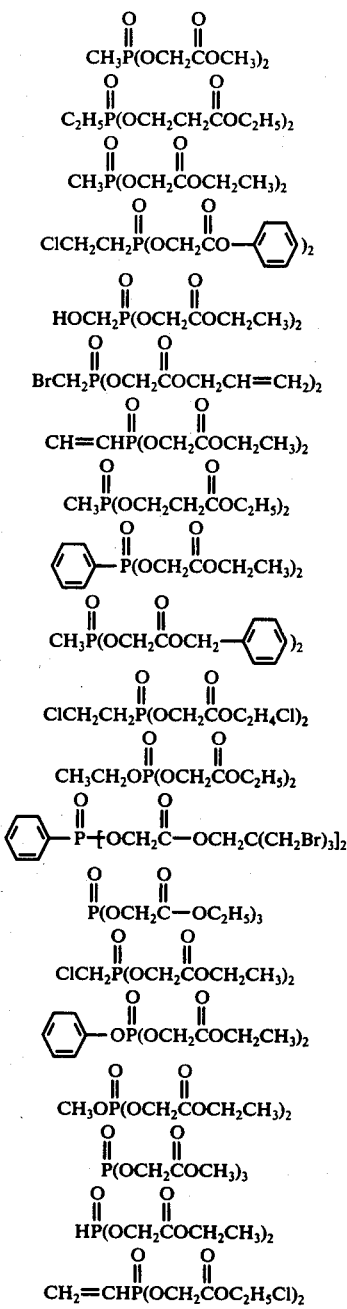

The products of the present invention are useful as flame retardants for polyurethane foams, unsaturated polyesters, acrylates, textiles, cellulosics, epoxy resins, aminoplasts and phenolics. In the manufacture of plastics, the products can be directly used as flame retardant components. For example, said products can transesterify into an unsaturated polyester alkyd composition, thereby becoming an integral part of the plastic.

The products also can be used as intermediates to make phosphorous oligomers. These oligomers, in turn, can be used as flame retardants, and because of their higher molecular weight will exhibit good durability.

The methods of preparing new polymeric compounds having the structural formula:

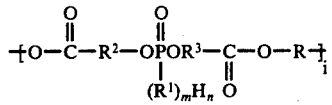
(VII)

wherein R, $R^1$, $R^2$ and $R^3$, and m and n are as described above and i is an integer from about 2 to about 20, are polycondensation or polymeric transalkylation.

Polycondensation comprises contacting a reactant having the structural formula (III) with a reactant selected from the group consisting of polyols having the structural formula:

$$R^7(OR^8)_g \quad \text{(VIII)}$$

wherein $R^7$ is hydrocarbyl consisting of hydrogen and carbon and substituted hydrocarbyl, and polyester; including $C_1$–$C_{20}$ alkylene and $C_7$–$C_{20}$ alkenylene, substituted arylene and derivatives of the foregoing containing non-labile pendant halogens, $C_1$–$C_6$ alkyls, $C_1$–$C_6$ haloalkyls, $C_2$–$C_6$ alkenyls and $C_2$–$C_6$ haloalkenyls. $R^8$ is selected from hydrogen and

where $R^2$ and X are as defined above. The integer represented by g is from about 1 to about 10.

Exemplary polyols of the formula (VIII) include but are not limited to the following:

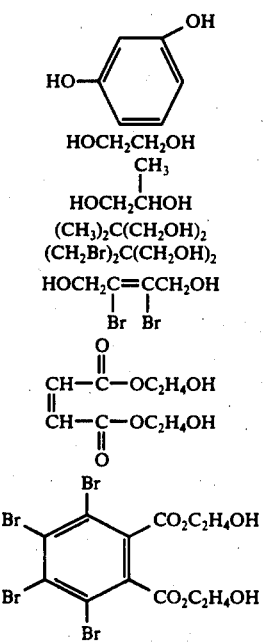

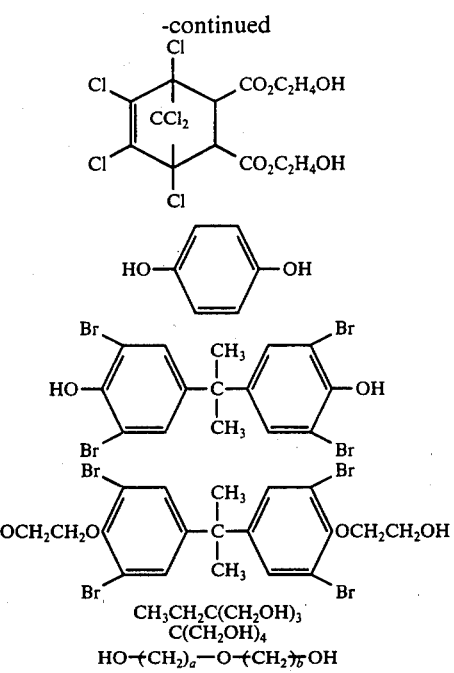

wherein a and b are the same or different and are integers from about 2 to about 4.

Other exemplary polyols of the formula (VIII) include sucrose polyether polyols and polyols of maleic acid, phthalic acid and ethylene glycol.

The reactants having the structural formalae (III) and (VIII) are contacted in the presence of a conventional transesterification catalyst such as stannous octoate, toluene sulfonic acid, manganese acetate, tetraalkyl titanoate, antimony oxide, tetraalkyl zirconate, ributoxy antimony, sulfuric acid, acidic clays, acidic sulfonic acid and ion exchange resins.

The equation representative of the polycondensation reaction is as follows:

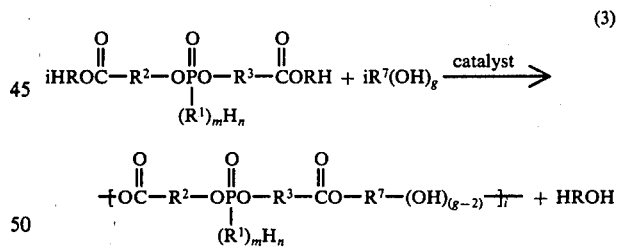
(3)

wherein R, $R^1 R^2 R^3$ and $R^7$ and m, n, g and i are as defined above.

While the molar ratio of phosphonate monomer to polyol will generally vary from about 0.5 to about 2.0, the preferred range for minimal byproduct formation is from about 0.8 to about 1.2.

A catalyst concentration ranging from about 0.001 to about 10% can be used. Generally, however, a range from about 0.05 to about 4.0% is employed for efficiency of catalyst function.

The polycondensation process of the present invention is generally carried out at a temperature of from about 100° C. to about 220° C. Temperatures of from about 150° C. to about 200° C. are preferred for a rapid transesterification rate consonant with keeping below the decomposition temperature of the reactants.

Reaction times can vary over relatively wide ranges and can easily be determined by one skilled in the art. Factors affecting reaction time include reactant and catalyst concentrations and temperature. Increases in temperature and catalyst concentration result in decreased reaction times. Dilute reactants require longer reaction times than concentrated reactants. Typical reaction times are from about 1 to about 12 hours.

The polycondensation method of the present invention can conveniently be effected by introducing the individual reactants and catalyst into any reaction zone that can be heated to the reaction temperature. The zone is generally provided with a condenser for removal of volatile components. A thermometer, thermocouple or other conventional means can be used to monitor temperature. The reaction can be carried out in a continuous or batch-type system as desired.

The products of the reaction are neutralized by treatment with an alkylene oxide such as ethylene oxide, epichlorohydrin, propylene oxide or a higher molecular weight diepoxide at about 50°–120° C. over a period of several hours. Catalysts such as stannous octoate and tributoxy antimony can accelerate this neutralization.

Devolatilization can be completed by application of a vacuum followed by passage of the products through a wiped-film evaporator or other similar types of equipment as are well-known in the art.

The identification of the products is generally achieved by elemental and infrared analysis or other suitable methods as are well known in the art.

The yield of the reaction is generally between about 85 and 95% of theoretical yield.

Another method, polymeric transalkylation, comprises contacting a phosphonate having the structural formula:

$$H_n-(R^1)_m\overset{\overset{O}{\|}}{P}(OR^6)_2 \quad (IV)$$

as defined above, with a dihalo bis(ester) reactant having the structural formula:

$$X-R^2-\overset{\overset{O}{\|}}{C}OR\overset{\overset{O}{\|}}{C}-R^3-X \quad (IX)$$

wherein $R$, $R^2$, $R^3$ and $X$ are as defined above, in the presence of a catalyst.

Exemplary phosphonates having the structural formula IV include but are not limited to the following:

$$CH_3\overset{\overset{O}{\|}}{P}(OCH_3)_2$$

$$CH_3\overset{\overset{O}{\|}}{P}(OCH_2CH_2Cl)_2$$

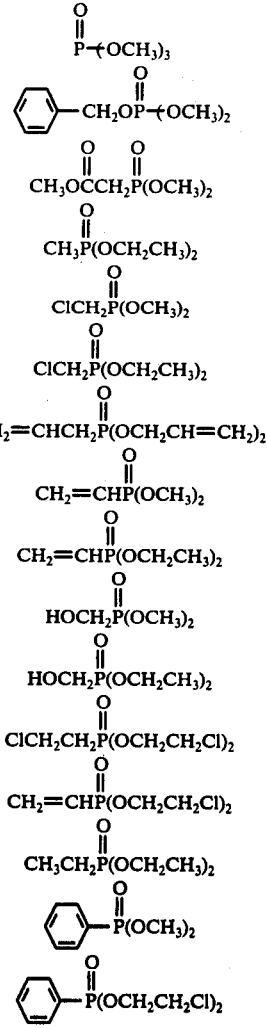

Exemplary dihalo bis(acetate) reactants having the structural formula IX include but are not limited to the following:

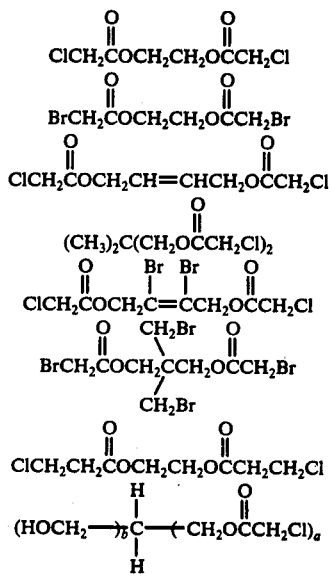

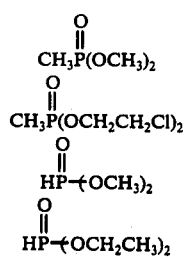

where $a+b=4$ and $a\geq 2$.

The catalyst is generally a nucleophilic salt such as tetraethyl ammonium chloride, sodium carbonate, sodium bicarbonate, lithium chloride and others.

The equation (4) representative of the polymeric transalkylation reaction is as follows:

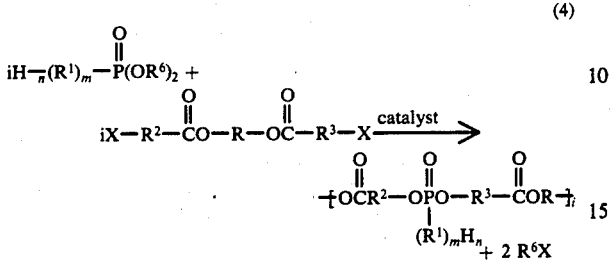

Molar reactant ratios of phosphonate to dihalo bis(esters) can vary from about 0.5 to about 2.0 although greater or lesser amounts can be used. Generally, reactant ratios ranging from about 0.8 to about 1.2 are used.

In equation (4), when $R^1$ is a pendant carboxylic acid function the polymer can be trifunctional.

The polymeric transalkylation process of the present invention is carried out at a temperature of from about 120° C. to about 230° C., and preferably from about 150° C. to about 190° C. for optimum reaction time and avoidance of product decomposition.

Reaction times can vary over relatively wide ranges and can easily be determined by one skilled in the art. Factors affecting reaction time include reactant and catalyst concentrations and temperature. Increases in temperature and catalyst concentration result in decreased reaction times. Dilute reactants require longer reaction times than concentrated reactants. Typical reaction times are from about 1 to about 10 hours.

The polymeric transalkylation method of the present invention can conveniently be effected by introducing the individual reactants and catalysts into a reaction zone that can be heated to the reaction temperature. The zone is generally provided with a condenser for removal of volatile components. A thermometer, thermocouple or other conventional means can be used to monitor temperature. The reaction can be carried out in a continuous or batch-type system as desired.

The products of the reaction are neutralized by treatment with an alkylene oxide such as ethylene oxide, epichlorohydrin, propylene oxide, or a higher molecular weight diepoxide over several hours at about 50°-120° C. Devolatilization is performed under reduced pressure followed by passage through a wiped-film evaporator or other similar types of equipment as are well known in the art.

The identification of the products is achieved by elemental and infrared analysis or other suitable methods as are well known in the art.

The yield of the reaction is generally between about 75 and 95% of theoretical yield.

Illustrative of the polymers which can be prepared by the methods of the present invention are:

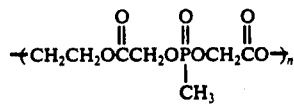

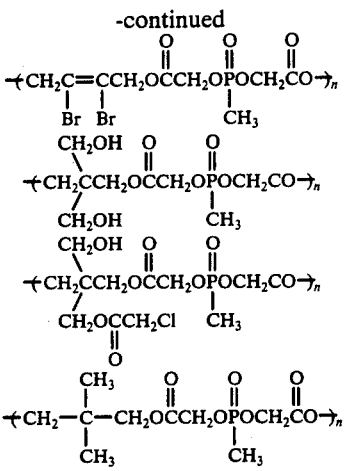

Unsaturated polyesters can be flame retarded by incorporation onto the backbone of the polyester alkyd of phosphonates having the structural formula:

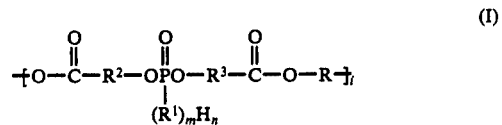

wherein $R$, $R^1$, $R^2$, $R^3$, $m$, $n$ and $i$ are as defined above. Such backbone incorporation gives permanency of the phosphorous flame retardant subsituent.

There are several procedures for accomplishing such incorporation and two are described herein.

In one method, the previously described phosphorus intermediate having structure:

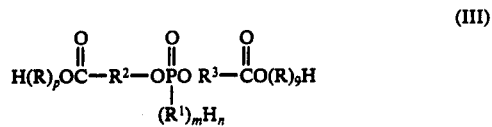

is condensed together with the general constituents of a polyester resin. Said resins generally comprise a mixture of glycols, e.g. propylene or diethylene glycol, unsaturated dibasic acids or anhydrides, e.g. fumaric acid or maleic anhydride, and, optionally, a saturated dibasic acid or anhydride, e.g. isophthalic, phthalic, chlorendic, bromated tetrahydrophthalic, tetrabromophthalic and tetrachlorophthalic acids and their respective anhydrides, which serves to control the reaction and modify the properties of the resulting product. These constituents are heated together in a combination having equivalent molar concentrations of alcohol and carboxy functionality. To the thus prepared fluid polyester, a reactive monomer, e.g. styrene, diallyl phthalate, diallyl isophthalate, methylmethacrylate or triallyl cyanurate, is then usually added and a peroxide catalyst, e.g. benzoyl peroxide, is introduced in order to catalyze the final copolymerization reaction. These polyesters, or unsaturated polyesters as they are often referred to, are thermosetting and are widely used in reinforced plastics and in the potting of electrical components.

In another procedure, chloroacetic acid is employed as one of the polyester components. Subsequent to polyesterification, a dialkyl, alkylphosphonate or a dialkyl arylphosphonate (e.g. dimethyl methylphosphonate) is made to transalkylate in situ with the chloroacetate end groups. This results in the formation of long chain or higher molecular weight crosslinked polyesters from smaller chain polyesters. A general equation for this would be:

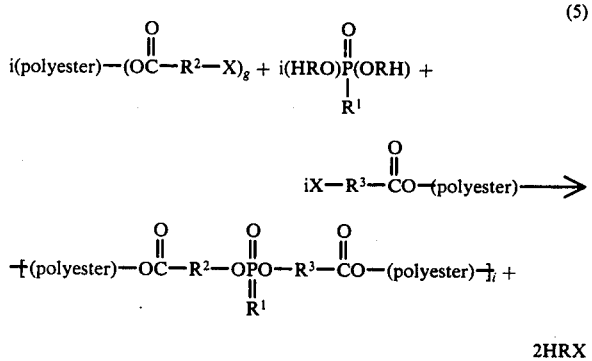

wherein $R$, $R^1$, $R^2$, $R^3$, $X$, $i$, and $g$ are as defined above, and the polyester is the residue derived from polyfunctional unsaturated or saturated acids (with or without halogen) and polyols.

The products of the present invention have numerous uses as illustrated in the following general outline:
1. lubricant additives
   a. anti-wear
   b. extreme pressure imparting
   c. antioxidant
   d. viscosity controlling
2. metal stabilizers
3. emulsifiers
4. surfactants
5. antistatic agents for textiles
6. flame retardants
   a. textiles
   b. plastics
   c. lubricants
7. plasticizers
8. antioxidants for plastics among others. Methods of using the products of the present invention for the foregoing utilities will be apparent to those skilled in the art on the basis of the present disclosure.

With respect to utilizing the products of the present invention to flame retard plastics, the following plastics are typical of those that can be used: unsaturated polyesters, cross-linked polyesters, polyacrylates, polymethacrylates, polyvinyl acetates, polyvinyl alcohols, polyvinylacetals, polyurethanes, polyisocyarates, polyureas, phenolic resins, cellulose acetates, cellulose butyrates, cellulose nitrate, epoxy resins, aminoplasts, (including aminoplasts such as urea-$CH_2O$, melamine-$CH_2O$, alkylated melamines and others) nylon, polyethylene terephthalate, polycarbonates, polyphenylene ethers, acrylonitrile butadiene styrene terpolymer, polystyrene, silicones, polyacrylonitrile, polyethylene, polypropylene, polyvinylchloride and others. Flame retardant amounts of the products of the present invention in plastics are generally in the range from about 0.2 percent to about 8 percent phosphorous by weight. The flame retardant plastics of the present invention can be produced by combining the products of the present invention with plastics by admixture or incorporation in the polymer backbone.

The present invention will be more fully illustrated in the Examples which follow:

EXAMPLE 1

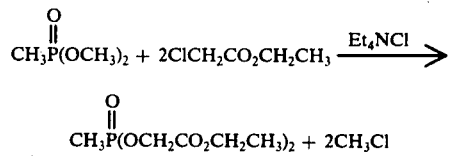

The monomer, bis(ethylacetoxy) methylphosphonate, was prepared by transalkylation. A reactor was charged with 620 g. (5.0 mole) of dimethyl methylphosphonate and 10 g. of tetraethylammonium chloride. The mixture was heated under nitrogen to 175° C. To this was added 1,372 g. (11.2 mole) ethyl chloroacetate over a 6 hour period while maintaining a pot temperature of 175° C. A further two hours at this temperature was required for reaction completion as noted by the collection of 490 g. (9.7 mole) of methyl chloride in a cold trap. The product was removed by distillation. A colorless liquid (1119 g., 4.15 mole, 83% yield) was recovered having a boiling point of 148° C./0.3 m. The H-nmr spectrum consisted of signals at $\tau$ 8.72 (6H, triplet, J=7 Hz, $OCH_2CH_3$), $\tau$8.39 (3H, doublet, J=19 Hz, $CH_3P$), $\tau$ 5.78 (4H, quartet, J=7Hz, $OCH_2CH_3$) and $\tau$5.42 (4H, doublet, J=12 Hz, $CH_2OP$). In the $^{31}$P-nmr spectrum a signal was observed at $-35$ ppm relative to ortho phosphoric acid. The observed phosphorus analysis was 11.7% which corresponds to the theoretical value of 11.5%.

EXAMPLE 2

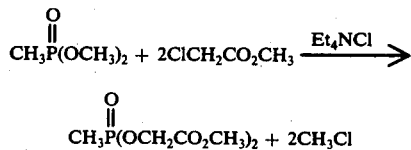

Bis(methylacetoxy) methylphosphonate was prepared as in the previous example. The reaction was charged with 248 g. (2.0 mole) of dimethyl methylphosphonate and 2 g. of tetraethylammonium chloride. Nitrogen was used to purge the system after which the contents were heated until reflux (177° C.). Methyl chloroacetate (504 g., 4.6 mole) was then added dropwise over a period of 3 hours at such a rate as to maintain the pot temperature between 165°–180°0 C. A $-78°$ C. cold trap leading from the reaction was found to contain 180 g. (3.55 mole) of methyl chloride by-product. Vacuum distillation of the pot mixture (bp 136°–140° C./0.6 mm) gave 312 g. (1.3 mole) of bis(methylacetoxy) methylphosphonate representing a 67% yield.

The $^1$H-nmr of this compound exhibited signals at $\tau$ 8.38 (3H, doublet, J=18 Hz, $CH_3O$), $\tau$ 6.26 (6H, singlet, $OCH_3$) and $\tau$ 5.38 (4H, doublet, J=12 Hz, $POCH_2$).

EXAMPLE 3A

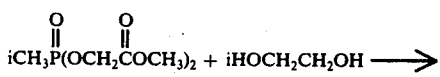

-continued

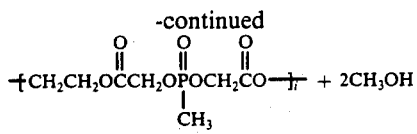

Polycondensation of bis(methylacetoxy) methylphosphonate (96 g., 0.40 mole) with ethylene glycol (24.8 g., 0.40 mole) was accomplished by heating these reagents at 180° C. for 3 hours in the presence of 0.3 g. stannous octoate. Methanol (16 g.) was continuously removed as it evolved from the reaction. A clear viscous liquid of acid number 12.3 mg. KOH/g. remained in the pot. Addition of ethylene oxide at 75° C. over several hours reduced the acid number to 0.56. Residual volatiles were removed by passing the product through a wiped-film evaporator (100° C./0.3 mm). Obtained were 88.7 g. of a clear white liquid having a phosphorus content of 11.8% and hydroxyl number of 159.

EXAMPLE 3B

As regards the previous example, other reactant concentration ratio polymers can be prepared in which final phosphorus content and hydroxyl functionality can be varied to suit the end application. For example, 96 g. (0.40 mole) of bis(methylacetoxy) methylphosphonate was transesterifed with 18.6 g. (0.30 mole) of ethylene glycol using 0.3 g. stannous octoate as catalyst. After heating for 4 hours at 163°–198° C. under nitrogen, a total of 12.9 g. methanol had evolved and been removed by distillation. Subsequently, ethylene oxide was bubbled slowly into the product at 75° C. over 5 hours to insure neutralization. Residual volatiles were removed by a 20 minute vacuum strip at 80°/18 mm, which was followed by passage of product through a wiped-film evaporator (100° C./0.3 mm). A clear, pale yellow, viscous liquid was thus obtained (84 g.). Analysis of this liquid indicated an acid number of 0.56, an hydroxyl number of 96 and a phosphorus content of 8.87%.

EXAMPLE 4

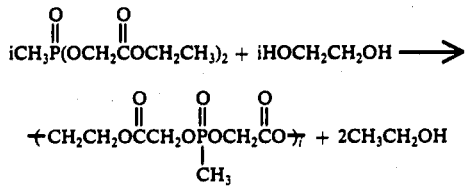

Polycondensation of bis(ethylacetoxy) methylphosphonate (134 g., 0.5 mole) with ethylene glycol (27.9 g., 0.45 mole) was accomplished by heating these reagents at 165°–180° C. for 4 hours in the presence of 0.3 g. stannous octoate under nitrogen. Ethanol (29.5 g.) was continuously removed as it evolved from the reaction. The product exhibited an acid number of 19 mg KOH/g at this junction. Neutralization was accomplished by treating the pot residue with ethylene oxide for several hours at 100° C. Residual volatiles were removed by first applying an aspirator vacuum for 30 minutes at 80° C. and then passing the product through a wiped-film evaporator (100° C/0.1 mm.). A yellow, semi-viscous liquid was obtained (100 g). Analysis revealed an acid number of 0.28, an hydroxyl number of 104 and a phosphorus content of 12.2%

EXAMPLE 5

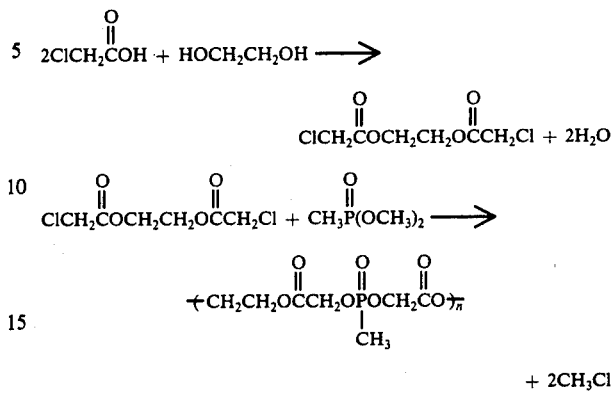

A typical esterification reactor apparatus, fitted with a Dean-Stark trap, was employed to condense 754 g (8.0 mole) of chloroacetic acid with 272 g (4.0 mole) of ethylene glycol. Stannous octoate (3.0 g) was used as catalyst while 35 ml of V, M and P naphtha was used as a water azeotrope solvent. The reactants were heated between 132°–165° C. under nitrogen. Condensation appeared complete after 7 hours as evidenced by the collection of 141.4 g. water relative to a theoretical value of 144 g. The product was diluted in 1500 ml methylene chloride and washed successively with water, aqueous sodium carbonate solution and water once again. The organic layer was separated, dried over MgSO$_4$ and solvent stripped on a rotary evaporator in vacuo. A clear, colorless liquid (710 g.) was obtained representing an 83% yield of the ethylene glycol bis-ester of chloroacetic acid.

Ethylene glycol bis-ester of chloroacetic acid (129 g., 0.60 mole) was reacted with 124 g. (1.0 mole) of dimethyl methylphosphonate using 0.5 g. of tetraethylammonium chloride as a catalyst. Transalkylation was performed at 164°–185° C. over a 4 hour period. A total of 56.2 g. (1.1 mole) of methyl chloride was recovered as by-product from an attached −78° C. cold trap. Neutralization of the product (acid number = 7.3 mg KPH/g) was accomplished by the addition of ethylene oxide over a two hour period at 100° C. Volatiles were stripped away under aspirator vacuum at 100° C. over a 30 minute interval. Next, the product was fed through a wiped-film evaporator (100° C./ 0.1 mm). Obtained were 142.5 g of a viscous orange fluid. The material had an acid number of 0.07, hydroxyl number of 36.9, phosphorus content of 14.0% and residual chlorine content of 0.39%.

EXAMPLE 6

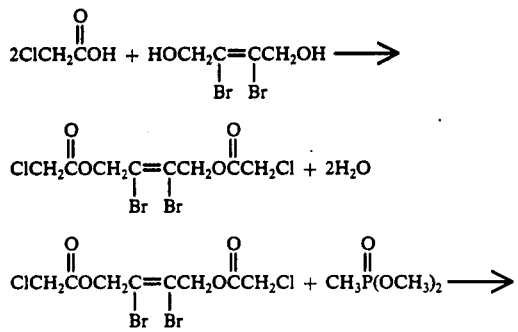

-continued

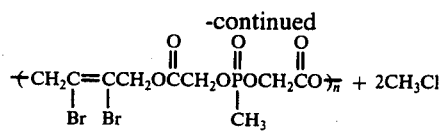

An esterification reactor fitted with a Dean-Stark trap was charged with 104 g (1.1 mole) of chloroacetic acid, 123 g (0.5 mole) of 1,4-dibromo-2-butenediol, 1 g stannous octoate and 80 ml V, M and P naphtha. The reactants were heated under nitrogen at 145°-153° C. After 14 hours, 17.0 g of hot water condensate had collected in the trap (theory=18 g). The product was diluted in 300 ml methylene chloride and washed successively with water, aqueous sodium carbonate and then water. The organic layer was separated, dried over $MgSO_4$ and solvent stripped in a rotatory evaporator in vacuo. A white solid weighing 172.6 g (0.87 mole) was obtained representing an 87% yeild. The crystals melted at 73°-74° C. An infrared spectrum indicated absence of OH but presence of bands at 3030, 3010 cm$^{-1}$ (C=C) and 1765 cm$^{-1}$ (C=O).

The dibromobutene diol bis-ester of chloracetic acid (60 g, 0.14 mole) was reacted with 49.6 g (0.40 mole) of dimethyl methylphosphonate in the presence of 0.5 g tetraethylammonium chloride as catalyst. Transalkylation was accomplished at 180°-205° C. over a 3 hour period. During the reaction 17.2 g (0.3 mole) of methyl chloride evolved and were collected in a −78° C. cold trap. The brown pot residue was dissolved in 150 ml methylene chloride and washed with two portions 200 ml water. After separating the organic layer, it was dried with $MgSO_4$. Solids were then filtered and solvent removed. A viscous liquid weighing 50.3 g was recovered.

EXAMPLE 7

A reactor was charged with 40.9 g (0.10 mole) of the dibromobutenediol bis-ester of chloroacetic acid, 14.9 g (0.12 mole) of dimethyl methylphosphonate and 0.2 g tetraethylammonium chloride. These reactants were heated at 205° C. over a 2 hour period. Methyl chloride by-product weighing 43.0 g was recovered from an attached cold trap. The product was taken up in methylene chloride and washed with water. After the usual work-up procedure, 43.0 g of a semi-solid remained.

EXAMPLE 13

Preparation of Control Resin.

A one-liter reactor kettle equipped with thermometer, stirrer, inert gas sparge tube, steam heated reflux column and total condenser was charged with 285.8 g. (1.0 mol) of tetrachlorophthalic anhydride, 89 g. (0.9 mol) of maleic anhydride, 124 g. (2.0 mol) of ethylene glycol and 0.1 g. of hydroquinone inhibitor. The reactants are heated slowly to 168° C. over a 7 hour period and then maintained at 195° C. for 11 hours. Throughout the reaction period, a slow stream of nitrogen is used to purge volatiles. Water of condensation (23.7 g.) was continuously removed through the heated reflux column and total condenser in a manner so that all the refluxing glycol was returned to the reactor. A pale yellow alkyd resin remained behind having an acid number of 21 mg. KOH/g. Upon cooling the alkyd resin down to 120° C., 216 g. of styrene containing 0.4 g, hydroquinone was added with efficient mixing to insure a homogeneous solution. Heat was then removed and the polyester allowed to cool; within 30 minutes the temperature had subsided to 80° C. The resultant resin contained by analysis 20.2% chlorine.

EXAMPLE 14

Preparation of phosphorus Containin Polyester by the In Situ Transalkylation of Chloroacetic Acid-Dimethyl Methylphosphnate The aforedescribed reactor was charged with 89 g.( 0.9 mol) of maleic anhydride, 285. 8 g. (1.0 mol) of tetrachlorophthalic anhydride, 94.5 g (1.0 mol) of chloracetic acid, 162 g. (2.6 mol) of ethylene glycol and 0.1 g of hydroquinone inhibitor. Heat was gradually applied to the reactants while a slow nitrogen stream assisted in the removal of water. Temperatures of 150° C., 170° C. and 190° C. were attained after 1.5, 5 and 7 hours, respectively. At the end of 13 hours a total of 52.8 g volatiles had been collected. One gram of tetraethylammonium chloride was now added, followed by 62 g (0.5 mol) of dimethyl methylphosphonate over a 15 minute period. A temperature of 190° C was maintained over a 4.5 hour period for this transalkylation step. By-product methyl chloride (46.1 g.) was continuously collected in a cold trap at =78° C. Subsequently, the reaction mixture was cooled to 110° C. The acid number was 2.2 mg.

Examples 8 – 12

End group variations of the polymer described in Example 5 can be made by changing reactant ratios. These examples are outlined in the following table:

| Examples | 8 | 9 | 10 | 11 | 12 |
|---|---|---|---|---|---|
| Reagents: | | | | | |
| Bis-ester (g., mole) | 215, 1.0 | 162, 0.75 | 108, 0.5 | 129, 0.6 | 129, 0.6 |
| Dimethyl methylphosphonate (g., mole) | 124, 1.0 | 124, 1.0 | 113, 0.9 | 149, 1.2 | 174, 1.4 |
| Tetraethylammonium chloride (g) | 1.0 | 0.5 | 0.5 | 0.5 | 0.5 |
| Conditions: | | | | | |
| Reaction Time (hours) | 2 | 3 | 3 | 4 | 3.3 |
| Reaction Temperature (° C.) | 161–175 | 162–175 | 152–181 | 178–190 | 150–166 |
| Acid Number: | | | | | |
| Before ethylene oxide treatment (mg KOH/g) | 8.4 | 5.6 | 5.6 | 7.8 | 5.6 |
| After ethylene oxide treatment (mg KOH/g) | 0.56 | 0.1 | 0.12 | 0.10 | 0.56 |
| Products: | | | | | |
| Methylchloride (g., mole) | 89, 1.1 | 65, 1.3 | 47, 0.93 | 57, 1.1 | 57, 1.1 |
| Residual polymer (g) | 238 | 175 | 117 | 177 | 163 |
| Analysis: | | | | | |
| Hydroxyl Number (mg KOH/g) | — | — | 36.8 | 53.2 | 80.1 |
| Phosphorus (%) | — | 12.9 | 14.0 | 14.3 | 14.5 |
| Chlorine (%) | — | 1.9 | 0.48 | 0.48 | 0.53 |

KOH/g. Styrene (216 g) containing 0.4 g hydroquinone was combined with the alkyd resin using vigorous stirring. The mixture was allowed to cool rapidly. A tan resin resulted having a phosphorus content of 2.2%.

EXAMPLE 15

Preparation of Phosphorus Containing Polyester Using Bis(ethylacetoxy) Methylphosphonate as Reactive Monomer Into a one-liter condensation-reaction equipped reactor were placed 285.8 g (1.0 mol) of tetrachlorophthalic anhydride, 49 g (0.5 mol) of maleic anhydride, 136.4 g (2.2 mol) of ethylene glycol, 134 g (0.5 mol) of bis(ethylacetoxy) methylphosphonate and 0.1 g of hydroquinone. These reagents were heated together at 165° –180° C. for 7 hours. Volatiles weighing 45.1 g were removed from the condensate. Subsequently, the alkyd resin, having an acid number of 76 mg (KOH/g was cooled to 80°C. Styrene (220 g) containing 0.6 g hydroquinone was blended into the alkyd resin. The product was a light yellow resin containing 2.2% phosphorus and 17.4% chlorine.

EXAMPLE 16

The synthesis of this polyester resin sampler was similar to that described in Example 14. Reagent quantities and product analysis is detailed in Table I.

EXAMPLE 17

This chlorendic acid based control resin was prepared in a manner similar to that described in Example 13. Reagent quantities and product analysis is detailed in Table I.

EXAMPLE 18

A chlorendic acid type resin was prepared incorporating phosphorus using bis (ethylacetoxy) methylphosphonate as a reactive monomer. The experimental details are similar to those of Example 15. See Table I for reagent quantities and product analysis.

EXAMPLE 19

The synthesis of this polyester resin sample was similar to that described in Example 14. Table I details reagent quantities and product analysis.

square foot fiberglass mat. Resin cure was catalysed with either a 1% methyl ethyl ketone peroxide - 0.1% dimethyl aniline promotor system or a 1% benzoyl peroxide - 0.1% dimethyl aniline promotor system. All samples were post-cured for 1 hour at 100° C.

Flammability of the polyester compositions was measured by the Oxygen Index Test and/or the HLT-15 test.

THE LIMTING OXYGEN INDEX TEST

This procedure, also known as the LOI method, is described by Fenimore and Martin in *Modern Plastics*, November, 1966. The LOI method directly relates flame retardancy to a measurement of the minimum percentage concentration of oxygen in an oxygen-nitrogen mixture which permits the sample to burn; the LOI being calculated as follows:

$$LOI = \frac{[O_2]}{[O_2] + [N_2]} \times 100$$

Thus, a higher LOI is indicative of a higher degree of flame retardancy.

The HLT-15 Flame Test

This test is conducted in a draft-free cabinet on 8 inches × ½ inch × ⅛ inch samples suspended vertically from the top. A bunsen burner flame 5 inches long with a 1½ inches long inner blue cone is inclined at an angle of 20° from the vertical so that the blue cone just touches the bottom tip of the sample. Five specimens of each sample are tested to the following schedule:

| Application | On Time (seconds) | Off Time |
|---|---|---|
| 1 | 5 | 10 |
| 2 | 7 | 14 |
| 3 | 10 | 20 |
| 4 | 15 | 30 |
| 5 | 25 | 50 |

A rating of 4 is assigned each time a sample extinguishes during the off time. A rating of 0 is assigned and testing ended on a specimen if it continues to burn beyond the alloted time. Should all five samples pass the 5 applications, a rating of 100 is attained. The elapsed Table I

| Example No. | Control 13 | 14 | 15 | 16 | Control 17 | 18 | 19 |
|---|---|---|---|---|---|---|---|
| % Cl | 20.2 | 18.0 | 17.4 | 11.7 | 22.5 | 19.2 | 22.6 |
| % P | | 2.2 | 2.2 | 5.0 | | 2.3 | 2.2 |
| Maleic Anhydride (mole) | 0.9 | 0.9 | 0.5 | 0.5 | 1.3 | 0.8 | 0.9 |
| Chlorendic Anhydrice (mole) | | | | | 0.7 | 0.7 | 0.7 |
| Tetrachlorophthalic Anhydride (mole) | 1.0 | 1.0 | 1.0 | 0.5 | | | |
| Chloroacetic Acid (mole) | | 1.0 | | 2.0 | | | 1.0 |
| Ethylene Glycol (mole) | 2.0 | 2.6 | 2.2 | 2.2 | 2.2 | 2.2 | 2.2 |
| Bis(ethylacetoxymethyl-phosphonate) (mole) | | | 0.5 | | | 0.5 | |
| Dimethyl methylphosphonate (mole) | | 0.5 | | 0.5 | | | 0.5 |
| Oxygen Index (%) | 26.1 | 29.8 | 28.1 | 29.1 | 25.5 | 30.3 | 29.1 |
| HLT-15 (Rating/Flame Time in seconds) | 60/— | 100/193 | 100/25 | | 24/— | 100/117 | 100/45 |

EXAMPLE 20

Polyester Evaluation

To evaluate the fire retardant properties of these polyester resins, ⅛ inch thick glass reinforced laminated panels were prepared from three layers of 1 ½ oz. per burning times are then summed in order to establish an additional rating of the sample.

As seen from Table 1, polyesters containing the acetoxy methylphosphonate linkages have Oxygen Index values 2-3% and 4-5% above those of the control tetrachlorophthalic anhydride and chlorendic anhydride based resins, respectively. Results of HLT-15 test also indicate significantly improved performance of acetoxy methylphosphonate containing polyester over control resins.

EXAMPLE 21

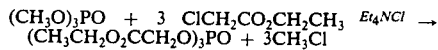
(CH₃O)₃PO + 3 ClCH₂CO₂CH₂CH₃ →^{Et₄NCl}
(CH₃CH₂O₂CCH₂O)₃PO + 3CH₃Cl

A reactor was charged with 140 g (1.0 mol) of trimethyl phosphate and 2 g of tetraethylammonium chloride. The mixture was heated until reflux. Ethyl chloroacetate (368 g, 3.0 mol) was added dropwise over a 5.5 hour period maintaining a temperature of 160°-180° C. throughout. After 15 hours, methyl chloride by-product evolution had ceased and the reaction was thus terminated.

A total of 135 g (2.7 mol) of methyl chloride had collected in an attached cold trap. The product was subsequently distilled under vacuum (bp 195° C.//0.20 mm) to give 190 g (0.52 mol) representing a 52% yield of tris(ethylacetoxy) phosphonate. The proton nmr of this substance exhibited signals at τ8.75 (9H, triplet J=7Hz, CH₃CH₂O) τ5.79 (6H, quartet J=7 Hz, CH₃CH₂O) and τ5.32 (6H, doublet J=11.5 Hz, COCH₂OP). Infrared bands at 1750 (C=O), 1290 and 1215 cm⁻¹ (P=O) were noted.

EXAMPLE 22

The use of the products described in Examples 3A and 3B as flame retardants for polyurethan foams is illustrated.

The foams were prepared by thoroughly mixing sequentially the materials, with the exception of TDI, as listed in Table III below. Toluene diisocyanate (TDI) was introduced last and the formulation mixed vigorously 5-10 seconds followed by a rapid pour into an 8 inch square cardboard box.

The degree of flame retardancy of the resulting foams was evaluated by the Motor Vehicle Safety Standard 302 Flammability Test (MVSS 302).

In this test, a specimen of foam 4 inches × ½ inch thick by 14 inches long is held horizontally between two U-shaped brackets which allow free access of air above and below. The specimen is ignited by a bunsen burner and the burning rate in inches/minute is measured. A burn rate below 4 inch/min. is usually required.

General Motors has an additional interpretation of MVSS 302:

| | |
|---|---|
| Does not ignite | DNI |
| SE before first mark (before 1 ½" total) | SE |
| SE in less than 3 ½" total | SE/NBR |
| SE after 3 ½" from starting point | SE, & burn rate |
| Burns full length | burn rate |

Results of these evaluations are presented in Table III.

TABLE III

| | | Foam | |
|---|---|---|---|
| Foam Components (in grams) | Control | No. 1 | No. 2 |
| Polyol CP3000 (a 3000 molecular weight triol from Dow Chemical Company) | 100 | 100 | 100 |
| Flame retardant from Example 3A | — | 10 | — |
| Flame retardant from Example 3B | — | — | 10 |
| Water | 4.5 | 4.5 | 4.5 |
| Silicone (Union Carbide L-548) | 1.0 | 1.0 | 1.0 |
| Amine (A 2:1 blend of N-ethylmorpholine and Union Carbide A-1 catalyst) | 0.3 | 0.3 | 0.3 |
| Tin (a 50% stannous octoate solution from American Can Company/called T-10) | 0.4 | 0.4 | 0.4 |
| Methylene chloride (blowing agent) | 3.0 | 3.0 | 3.0 |
| TDI (an 80/20 mixture of 2,4- and 2,6-toluene diisocyanate) | 60 | 60 | 60 |
| MVSS 302 Text | Burns (4.5"/min.) | SE/NBR | SE |

Not only were the materials from Example 3A and 3B good flame retardants as seen above but the resultant foams possessed excellent physical properties. Moreover, the tendency to cause scorch exhibited by many flame retardants was virtually eliminated with these materials.

Having set forth the general nature and some examples of the present invention, the scope is now particularly set forth in the appended claims.

What is claimed is:

1. A compound having the formula:

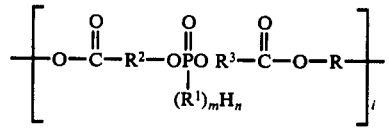

wherein R is selected from the group consisting of C₂-C₁₀ alkylene, arylene, C₇-C₂₀ alkylene substituted arylene, C₃-C₂₀ cycloalkylene, C₄-C₂₀ vinylene and derivatives of the foregoing containing non-labile pendant halogens, C₁-C₆ alkyl groups, C₁-C₆ haloalkyl groups, vinyl groups, ether groups and C₁-C₆ alkyl alcohol groups; R¹ is selected from the group consisting of C₁-C₁₀ alkyl, aryl, C₇-C₂₀ alkyl substituted aryl, C₂-C₁₀ alkenyl, phenoxy, C₁-C₁₀ alkoxy, aryloxy, and C₃-C₂₀ cycloalkyl, and derivatives thereof containing non-labile pendant halogens, C₁-C₆ alkyl groups, C₁-C₆ haloalkyl groups, vinyl groups, ether groups, and C₁-C₆ alkyl alcohol groups and

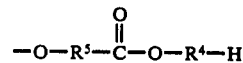

and OR⁴H wherein R⁴ has the same definitions as R, and R⁴ and R can be the same or different; R², R³ and R⁵ are straight or branched C₁-C₁₀ alkylene and can be the same or different; i is an integer from about 2 to about 20; the integers represented by m and n are different and are 0 to 1.

2. The compound of claim 1 wherein R is selected from the group consisting of ethylene, chloroethylene, vinylene, propylene, bromopropylene, propenylene, isopropylene, butylene, butenylene, hydroxybutylene, isobutylene, chlorobutenylyne, pentylene, hexylene, octylene, hydroxyoctylene, decylene, cyclopentylene, cyclohexylene, hydroxycyclopentylene, phenylene, methylphenylene, and chlorophenylene.

3. The compound of claim 1 wherein $R^1$ is selected from the group consisting of methyl, chloromethyl, hydroxymethyl, ethyl, chloroethyl, hydroxyethyl, vinyl, propyl, bromopropyl, propenyl, isopropyl, butyl, butenyl, hydroxybutyl, isobutyl, chlorobutyl, pentyl, hexyl, octyl, hydroxyoctyl, decyl, cyclopentyl, cyclohexyl, hydroxycyclopentyl, phenyl, methylphenyl, chlorophenyl, carbalkoxymethyl and carbalkoxyethyl.

4. The compound of claim 1 wherein $R^2$, $R^3$ and $R^5$ are the same or different and are selected from the group consisting of methylene, ethylene, propylene, isopropylene, butylene, isobutylene, tert-butylene, pentylene, hexylene, heptylene, octylene, nonylene and decylene.

* * * * *